(12) United States Patent
Wilson et al.

(10) Patent No.: US 9,695,316 B2
(45) Date of Patent: Jul. 4, 2017

(54) CYCLIC SILOXANE COMPOUNDS AND COMPOSITIONS COMPRISING THE SAME

(71) Applicant: MILLIKEN & COMPANY, Spartanburg, SC (US)

(72) Inventors: Michael E. Wilson, Middleburg, FL (US); Yuzhou Liu, Beijing (CN); Sharon E. Koh-Fallet, Crofton, MD (US); Yunzhang Wang, Duncan, SC (US); Sudhanshu Srivastava, Greer, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 15/148,238

(22) Filed: May 6, 2016

(65) Prior Publication Data

US 2016/0340511 A1 Nov. 24, 2016

Related U.S. Application Data

(60) Provisional application No. 62/163,082, filed on May 18, 2015, provisional application No. 62/197,791, filed on Jul. 28, 2015.

(51) Int. Cl.
| | | |
|---|---|---|
| *C08L 83/04* | (2006.01) | |
| *C07F 7/21* | (2006.01) | |
| *C08G 77/04* | (2006.01) | |

(52) U.S. Cl.
CPC ............ *C08L 83/04* (2013.01); *C07F 7/21* (2013.01); *C08G 77/04* (2013.01)

(58) Field of Classification Search
None
See application file for complete search history.

(56) References Cited

U.S. PATENT DOCUMENTS

| | | | | |
|---|---|---|---|---|
| 3,297,632 A | | 1/1967 | Wu | |
| 3,629,359 A | * | 12/1971 | Nitzsche et al. | C08L 83/04 528/23 |
| 4,077,994 A | * | 3/1978 | Davies | C08G 77/045 556/417 |
| 4,497,943 A | * | 2/1985 | Takago | C07F 7/0818 524/780 |
| 5,298,589 A | * | 3/1994 | Buese | C07F 7/21 525/477 |
| 5,330,836 A | * | 7/1994 | Buese | C08K 9/06 106/490 |
| 5,347,028 A | | 9/1994 | Buese et al. | |
| 5,693,735 A | * | 12/1997 | Sugo | C07F 7/21 528/14 |
| 5,700,899 A | * | 12/1997 | Aoki | C08G 77/04 521/31 |
| 6,284,906 B1 | * | 9/2001 | Paulasaari | C07F 7/21 528/12 |
| 6,291,623 B1 | * | 9/2001 | Paulasaari | C08G 77/24 528/25 |
| 7,388,065 B2 | | 6/2008 | Kennedy et al. | |
| 2002/0132408 A1 | * | 9/2002 | Ma | C09D 4/00 438/200 |
| 2006/0041098 A1 | | 2/2006 | Kennedy et al. | |
| 2006/0128922 A1 | * | 6/2006 | Daum | C08G 77/08 528/37 |
| 2008/0097064 A1 | | 4/2008 | Blanc-Magnard et al. | |
| 2013/0079539 A1 | | 3/2013 | Wilson et al. | |
| 2014/0306259 A1 | | 10/2014 | Liu et al. | |
| 2014/0309448 A1 | | 10/2014 | Liu et al. | |
| 2014/0309450 A1 | | 10/2014 | Liu | |

FOREIGN PATENT DOCUMENTS

SU 410023 A1 1/1974

OTHER PUBLICATIONS

Makarova, M.N. et al., "Synthesis and Thermal Decomposition of Methylsiloxane Oligomers Containing Two Linked Cyclosiloxane Units," Polyhedron vol. 2, No. 4, pp. 257-260, 1983.
PCT/US2016/031173 International Search Report, filed May 6, 2016, 5 pages.
PCT/US2016/031173 Written Opinion of the International Searching Authority, filed May 6, 2016, 8 pages.

* cited by examiner

*Primary Examiner* — Robert S Loewe
(74) *Attorney, Agent, or Firm* — Robert M. Lanning

(57) ABSTRACT

A siloxane compound conforms to the structure of one of Formulae (I), (X), and (XX). A composition comprises (a) a first siloxane compound selected from the group consisting of compounds conforming to the structure of Formula (X) and compounds conforming to the structure of Formula (XX) and (b) a second siloxane compound, the second siloxane compound comprising a plurality of siloxane repeating units, including cyclotrisiloxane repeating units conforming to the structure of Formula (XL).

38 Claims, No Drawings

CYCLIC SILOXANE COMPOUNDS AND COMPOSITIONS COMPRISING THE SAME

CROSS-REFERENCE TO RELATED PATENT APPLICATIONS

This application claims, pursuant to 35 U.S.C. §119(e)(1), priority to and the benefit of the filing date of U.S. Patent Application No. 62/163,082 filed on May 18, 2015 and U.S. Patent Application No. 62/197,791 filed on Jul. 28, 2015 which applications are hereby incorporated by reference in their entirety.

TECHNICAL FIELD OF THE INVENTION

This application relates to cyclic siloxane compounds, compositions comprising cyclic siloxane compounds, methods for making such compounds and compositions, and methods for using such compounds and compositions.

BACKGROUND

Siloxane compounds and silicones have found many uses in modern industry. For example, siloxane compounds are widely used in the production of cross-linked silicone polymers. These polymers typically are produced by either a hydrosilylation reaction or a condensation reaction. In the hydrosilylation reaction, siloxane compounds bearing vinyl groups undergo addition to link individual molecules of the compounds through the formation of new Si—C bonds. The hydrosilylation reaction typically is catalyzed by platinum, which contributes to the cost of these polymers because the platinum cannot be recovered from the cured elastomer. In the condensation reaction, the siloxane compounds react in a condensation reaction to form new Si—O—Si linkages between individual molecules. This condensation reaction produces volatile organic compounds (VOCs) as a by-product.

Cross-linked silicone polymers can be used as sealants or encapsulants for electronics. In particular, cross-linked silicone polymers can be used as encapsulants for light emitting diodes (LEDs). These cross-linked silicone polymers are desirable because they do not interfere with the operation of the electronic components. However, the cross-linked silicone polymers that exhibit sufficiently high temperature stability to be used as encapsulants for higher power LEDs do not have a high refractive index. This lower refractive index means that the light output from the LED will be reduced due to internal reflections in the semiconductor die of the LED.

A need remains for siloxane compounds that are suitable for use in making cross-linked silicone polymers without generating a large amount of volatile reaction products, such as the carbon-containing VOC's produced by condensation cure cross-linked silicone polymers. A need also remains for siloxane compounds and cross-linked silicone polymers that exhibit a high refractive index and are therefore better suited for use in those applications that demand an encapsulant material exhibiting a high refractive index (e.g., LED encapsulant applications). A need also remains for processes for generating these siloxane compounds and cross-linked silicone polymers. The subject matter described in the present application seeks to address these and other needs.

BRIEF SUMMARY OF THE INVENTION

In a first embodiment, the invention provides a compound conforming to the structure of Formula (I) below

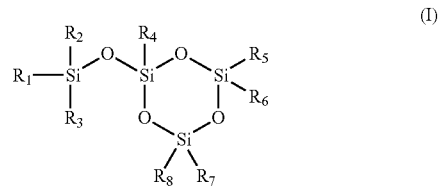

(I)

wherein $R_1$ is selected from the group consisting of hydrogen and —$OR_9$; $R_9$ is selected from the group consisting of hydrogen, alkyl groups, and substituted alkyl groups; and $R_2$, $R_3$, $R_4$, $R_5$, $R_6$, $R_7$, and $R_8$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$.

In a second embodiment, the invention provides a compound conforming to the structure of Formula (X) below

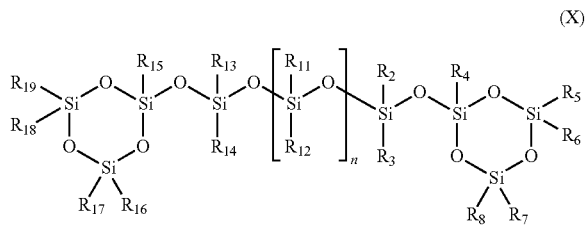

(X)

wherein $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$ and at least one of $R_{16}$ and $R_{17}$ is different from each of $R_{13}$, $R_{14}$, $R_{15}$, $R_{18}$, and $R_{19}$; and n is selected from the group consisting of integers equal to or greater than 1.

In a third embodiment, the invention provides a compound conforming to the structure of Formula (XX) below

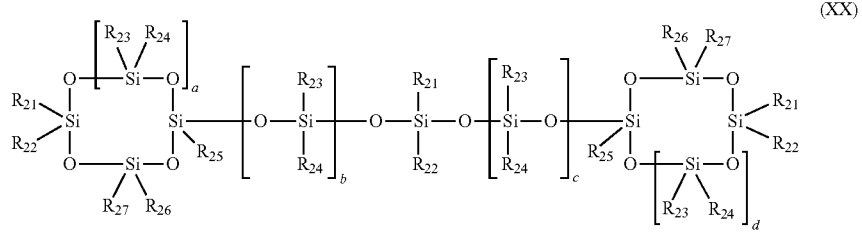

(XX)

wherein a, b, c, and d are integers selected from the group consisting of 0 and 1; the sum of a and b is equal to 1; the

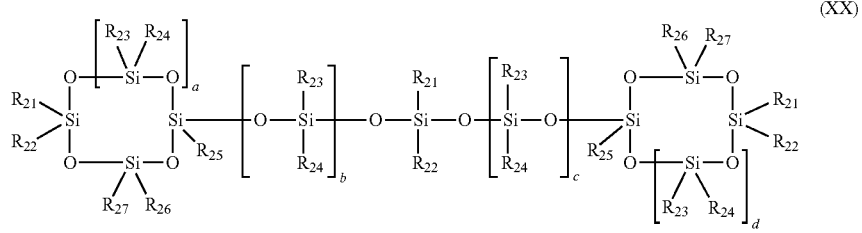

(XX)

sum of c and d is equal to 1; and $R_{21}$, $R_{22}$, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_{21}$ and $R_{22}$ is different from each of $R_{23}$, $R_{24}$, $R_{25}$, $R_{26}$, and $R_{27}$.

In a fourth embodiment, the invention provides a composition comprising:

(a) a first siloxane compound selected from the group consisting of compounds conforming to the structure of Formula (X) and compounds conforming to the structure of Formula (XX), wherein the structure of Formula (X) is

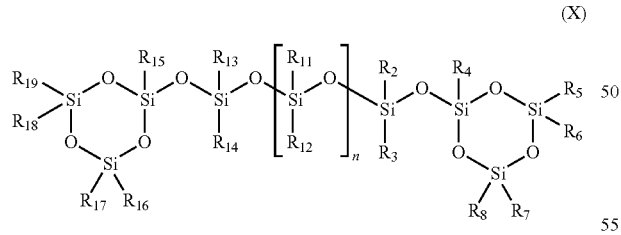

(X)

wherein $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$ and at least one of $R_{16}$ and $R_{17}$ is different from each of $R_{13}$, $R_{14}$, $R_{15}$, $R_{18}$, and $R_{19}$;

and n is selected from the group consisting of integers equal to or greater than 1; and the structure of Formula (XX) is wherein a, b, c, and d are integers selected from the group consisting of 0 and 1; the sum of a and b is equal to 1; the sum of c and d is equal to 1; and $R_{21}$, $R_{22}$, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_{21}$ and $R_{22}$ is different from each of $R_{23}$, $R_{24}$, $R_{25}$, $R_{26}$, and $R_{27}$; and (b) a second siloxane compound, wherein the second siloxane compound comprises a plurality of siloxane repeating units, about 10 mol. % or more of the siloxane repeating units are cyclotrisiloxane repeating units, the cyclotrisiloxane repeating units are independently selected from the group consisting of cyclotrisiloxane repeating units conforming to the structure of Formula (XL) below:

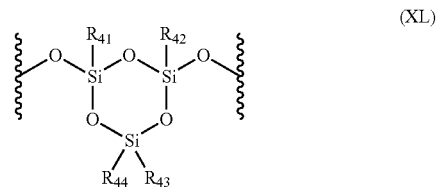

(XL)

wherein $R_{41}$ and $R_{42}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_{43}$ and $R_{44}$ are independently selected from the group consisting of haloalkyl groups, aralkyl groups, aryl groups, substituted aryl groups, heteroaryl groups, and substituted heteroaryl groups.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom, a nitrogen atom, or a sulfur atom.

As used herein, the term "alkenyl groups" refers to univalent functional groups derived from acyclic, unbranched and branched olefins (i.e., hydrocarbons having one or more carbon-carbon double bonds) by removal of a hydrogen atom from a carbon atom of the olefin.

As used herein, the term "substituted alkenyl groups" refers to univalent functional groups derived from acyclic, substituted olefins by removal of a hydrogen atom from a carbon atom of the olefin. In this definition, the term "substituted olefins" refers to compounds derived from acyclic, unbranched and branched hydrocarbons having one or more carbon-carbon double bonds in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "cycloalkenyl groups" refers to univalent functional groups derived from cyclic olefins (i.e., non-aromatic, monocyclic and polycyclic hydrocarbons having one or more carbon-carbon double bonds) by removal of a hydrogen atom from a carbon atom of the olefin. The carbon atoms in the cyclic olefins can be substituted with alkyl groups and/or alkenyl groups.

As used herein, the term "substituted cycloalkenyl groups" refers to univalent functional groups derived from substituted cyclic olefins by removal of a hydrogen atom from a carbon atom of the cyclic olefin. In this definition, the term "substituted cyclic olefins" refers to compounds derived from non-aromatic, monocyclic and polycyclic hydrocarbons having one or more carbon-carbon double bonds in which one or more of the hydrogen atoms of the hydrocarbon is replaced with a non-hydrogen atom (e.g., a halogen atom) or a non-alkyl functional group (e.g., hydroxy group, aryl group, heteroaryl group).

As used herein, the term "heterocyclyl groups" refers to univalent functional groups derived from heterocyclic compounds by removal of a hydrogen atom from an atom in the cyclic portion of the heterocyclic compound. In this definition, the term "heterocyclic compounds" refers to compounds derived from non-aromatic, monocyclic and polycyclic compounds having a ring structure composed of atoms of at least two different elements. These heterocyclic compounds can also comprise one or more double bonds.

As used herein, the term "substituted heterocyclyl groups" refers to univalent functional groups derived from substituted heterocyclic compounds by removal of a hydrogen atom from an atom in the cyclic portion of the compound. In this definition, the term "substituted heterocyclic compounds" refers to compounds derived from non-aromatic, monocyclic and polycyclic compounds having a ring structure composed of atoms of at least two different elements where one or more of the hydrogen atoms of the cyclic compound is replaced with a non-hydrogen atom (e.g., a halogen atom) or a functional group (e.g., hydroxy group, alkyl group, aryl group, heteroaryl group). These substituted heterocyclic compounds can also comprise one or more double bonds.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., hydroxy group).

As used herein, the term "substituted heteroaryl groups" refers to univalent functional groups derived from substituted heteroarenes by removal of a hydrogen atom from a ring carbon atom. In this definition, the term "substituted heteroarenes" refers to compounds derived from monocyclic and polycyclic aromatic hydrocarbons in which (1) one or more of the hydrogen atoms of the hydrocarbon is replaced with a non-hydrogen atom (e.g., a halogen atom) or a non-alkyl functional group (e.g., hydroxy group) and (2) at least one methine group (—C=) of the hydrocarbon is replaced by a trivalent heteroatom and/or at least one vinylidene group (—CH=CH—) of the hydrocarbon is replaced by a divalent heteroatom.

As used herein, the term "alkanediyl groups" refers to divalent functional groups derived from alkanes by removal of two hydrogen atoms from the alkane. These hydrogen atoms can be removed from the same carbon atom on the alkane (as in ethane-1,1-diyl) or from different carbon atoms (as in ethane-1,2-diyl).

As used herein, the term "substituted alkanediyl groups" refers to divalent functional groups derived from substituted alkanes by removal of two hydrogen atoms from the alkane. These hydrogen atoms can be removed from the same carbon atom on the substituted alkane (as in 2-fluoroethane-1,1-diyl) or from different carbon atoms (as in 1-fluoroethane-1,2-diyl). In this definition, the term "substituted alkanes" has the same meaning as set forth above in the definition of substituted alkyl groups.

As used herein, the term "alkenediyl groups" refers to divalent functional groups derived from acyclic, unbranched and branched olefins (i.e., hydrocarbons having one or more carbon-carbon double bonds) by removal of two hydrogen atoms from the olefin. These hydrogen atoms can be removed from the same carbon atom on the olefin (as in but-2-ene-1,1-diyl) or from different carbon atoms (as in but-2-ene-1,4-diyl).

As used herein, the term "acyl groups" refers to univalent functional groups derived from alkyl carboxylic acids by removal of a hydroxy group from a carboxylic acid group. In this definition, the term "alkyl carboxylic acids" refers to acyclic, unbranched and branched hydrocarbons having one or more carboxylic acid groups.

As used herein, the term "substituted acyl groups" refers to univalent functional groups derived from substituted alkyl carboxylic acids by removal of a hydroxy group from a carboxylic acid group. In this definition, the term "substituted alkyl carboxylic acids" refers to compounds having one or more carboxylic acid groups bonded to a substituted alkane, and the term "substituted alkane" is defined as it is above in the definition of substituted alkyl groups.

As used herein, the term "siloxy groups" refers to univalent functional groups having the structure —[OSiR$_x$R$_y$]$_g$R$_z$, where R$_x$, R$_y$, and R$_z$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups and the variable g is an integer equal to or greater than 1. In a preferred embodiment, R$_x$, R$_y$, and R$_z$ are independently selected from the group consisting of alkyl groups (e.g., C$_1$-C$_8$ alkyl groups), and the variable g is an integer from 1 to 50, more preferably 1 to 20.

In a first embodiment, the invention provides a compound conforming to the structure of Formula (I) below

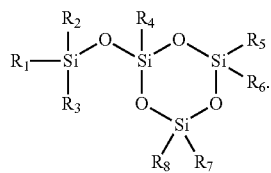

(I)

In the structure of Formula (I), R$_1$ is selected from the group consisting of hydrogen and —OR$_9$. R$_9$ is selected from the group consisting of hydrogen, alkyl groups, and substituted alkyl groups. R$_2$, R$_3$, R$_4$, R$_5$, R$_6$, R$_7$, and R$_8$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups. At least one of R$_7$ and R$_8$ is different from each of R$_2$, R$_3$, R$_4$, R$_5$, and R$_6$.

In a preferred embodiment, R$_1$ is —OR$_9$. The group R$_9$ preferably is an alkyl group, with C$_1$-C$_8$ alkyl groups being particularly preferred. In a particularly preferred embodiment, R$_9$ is a methyl group.

In another preferred embodiment, R$_2$, R$_3$, R$_4$, R$_5$, and R$_6$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups. More preferably, R$_2$, R$_3$, R$_4$, R$_5$, and R$_6$ are independently selected from the group consisting of alkyl groups and substituted alkyl groups, with C$_1$-C$_8$ alkyl groups and C$_1$-C$_8$ substituted alkyl groups being particularly preferred. More preferably, R$_2$, R$_3$, R$_4$, R$_5$, and R$_6$ are independently selected from the group consisting of alkyl groups, with C$_1$-C$_8$ alkyl groups being particularly preferred. In a particularly preferred embodiment, R$_2$, R$_3$, R$_4$, R$_5$, and R$_6$ are methyl groups.

In another preferred embodiment, R$_7$ and R$_8$ are independently selected from the group consisting of haloalkyl groups, aralkyl groups, aryl groups, substituted aryl groups, heteroaryl groups, and substituted heteroaryl groups. More preferably, R$_7$ and R$_8$ are independently selected from the group consisting of aryl groups, substituted aryl groups, heteroaryl groups, and substituted heteroaryl groups, with C$_6$-C$_{10}$ aryl groups, C$_6$-C$_{12}$ substituted aryl groups, C$_4$-C$_{10}$ heteroaryl groups, and C$_4$-C$_{12}$ substituted heteroaryl groups being particularly preferred. More preferably, R$_7$ and R$_8$ are independently selected from the group consisting of aryl groups and substituted aryl groups, with C$_6$-C$_{10}$ aryl groups and C$_6$-C$_{12}$ substituted aryl groups being particularly preferred. More preferably, R$_7$ and R$_8$ are independently selected from the group consisting of aryl groups, with C$_6$-C$_{10}$ aryl groups being particularly preferred. In a particularly preferred embodiment, R$_7$ and R$_8$ are phenyl groups.

In a particularly preferred embodiment, R$_1$ is —OR$_9$, R$_2$, R$_3$, R$_4$, R$_5$, and R$_6$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups, and R$_7$ and R$_8$ are independently selected from the group consisting of haloalkyl groups, aralkyl groups, aryl groups, substituted aryl groups, heteroaryl groups, and substituted heteroaryl groups. In a more specific embodiment, R$_1$ is —OR$_9$, R$_9$ is an alkyl group, R$_2$, R$_3$, R$_4$, R$_5$, and R$_6$ are independently selected from the group consisting of alkyl groups and substituted alkyl groups, and R$_7$ and R$_8$ are independently selected from the group consisting of aryl groups, substituted aryl groups, heteroaryl groups, and substituted heteroaryl groups. In yet another specific preferred embodiment, R$_1$ is —OR$_9$, R$_9$ is a C$_1$-C$_8$ alkyl group, R$_2$, R$_3$, R$_4$, R$_5$, and R$_6$ are independently selected from the group consisting of C$_1$-C$_8$ alkyl groups and C$_1$-C$_8$ substituted alkyl groups, and R$_7$ and R$_8$ are independently selected from the group consisting of C$_6$-C$_{10}$ aryl groups, C$_6$-C$_{12}$ substituted aryl groups, C$_4$-C$_{10}$ heteroaryl groups, and C$_4$-C$_{12}$ substituted heteroaryl groups. In another specific preferred embodiment, R$_1$ is —OR$_9$, R$_9$ is an alkyl group, R$_2$, R$_3$, R$_4$, R$_5$, and R$_6$ are independently selected from the group consisting of alkyl groups, and R$_7$ and R$_8$ are independently selected from the group consisting of aryl groups and substituted aryl groups. In another specific preferred embodiment, R$_1$ is —OR$_9$, R$_9$ is a C$_1$-C$_8$ alkyl group, R$_2$, R$_3$, R$_4$, R$_5$, and R$_6$ are independently selected from the group consisting of C$_1$-C$_8$ alkyl groups, and R$_7$ and R$_8$ are independently selected from the group consisting of C$_6$-C$_{10}$ aryl groups and C$_6$-C$_{12}$ substituted aryl groups. In another specific preferred embodiment, R$_1$ is —OR$_9$, R$_9$ is an alkyl group, R$_2$, R$_3$, R$_4$, R$_5$, and R$_6$ are independently selected from the group consisting of alkyl groups, and R$_7$ and R$_8$ are independently selected from the group consisting of aryl groups. In another specific preferred embodiment, $R_1$ is —$OR_9$, $R_9$ is a $C_1$-$C_8$ alkyl group, $R_2$, $R_3$, $R_4$, $R_5$, and $R_6$ are independently selected from the group consisting of $C_1$-$C_8$ alkyl groups, and $R_7$ and $R_8$ are independently selected from the group consisting of $C_6$-$C_{10}$ aryl groups. In yet another specific preferred embodiment, $R_1$ is —$OR_9$, $R_9$ is a methyl group, $R_2$, $R_3$, $R_4$, $R_5$, and $R_6$ are methyl groups, and $R_7$ and $R_8$ are phenyl groups.

The compound conforming to the structure of Formula (I) can be synthesized by any suitable process. For example, the compound can be synthesized by reacting approximately equimolar amounts of a hydrosiloxane compound conforming to the structure of Formula (IA) below

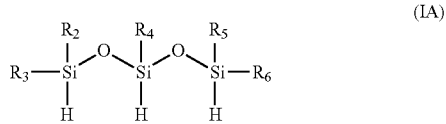

with a silane compound conforming to the structure of Formula (IB) below

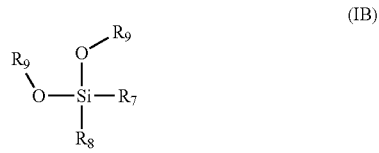

in the presence of a suitable Lewis acid catalyst. In the structures of Formulae (IA) and (IB), the groups $R_1$, $R_2$, $R_3$, $R_4$, $R_5$, $R_6$, $R_7$, $R_8$, and $R_9$ are selected from the same groups recited above for the structure of Formula (I). Preferably, each $R_9$ is a hydrogen. The Lewis acid catalyst used in the reaction preferably is a triphenylborane compound, such as a triphenylborane compound having the formula $B(C_6H_yX_{5-y})_3$ in which y is an integer from 0 to 5, each X is independently selected from the group consisting of F, $OCF_3$, $SCF_3$, R', and OR', and each R' is independently selected from the group consisting of H, $C_1$-$C_{22}$ alkyl, and $C_6$-$C_{22}$ aryl. In a preferred embodiment, the Lewis acid catalyst is tris(pentafluorophenyl)borane. The reaction between the compound of Formula (IA) and the compound of Formula (IB) yields a compound conforming to the structure of Formula (I) in which $R_1$ is hydrogen. If desired, the —SiH group present in this compound can be reacted with a suitable aldehyde compound to produce a compound in which $R_1$ is —$OR_9$.

In a second embodiment, the invention provides a compound conforming to the structure of Formula (X) below

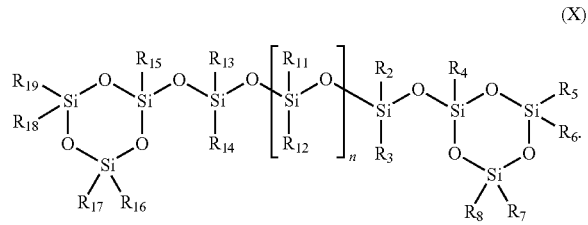

In the structure of Formula (X), $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups. At least one of $R_7$ and $R_8$ is different from each of $R_2$, $R_3$, $R_4$, $R_5$, and $R_6$, and at least one of $R_{16}$ and $R_{17}$ is different from each of $R_{13}$, $R_{14}$, $R_{15}$, $R_{18}$, and $R_{19}$. The variable n is selected from the group consisting of integers equal to or greater than 1.

In a preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups. More preferably, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups and substituted alkyl groups, with $C_1$-$C_8$ alkyl groups and $C_1$-$C_8$ substituted alkyl groups being particularly preferred. More preferably, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups, with $C_1$-$C_8$ alkyl groups being particularly preferred. In a particularly preferred embodiment, $R_2$, $R_3$, $R_4$, $R_5$, $R_6$, $R_{13}$, $R_{14}$, $R_{15}$, $R_{18}$, and $R_{19}$ are methyl groups.

In another preferred embodiment, $R_7$, $R_8$, $R_{16}$, and $R_{17}$ are independently selected from the group consisting of haloalkyl groups, aralkyl groups, aryl groups, substituted aryl groups, heteroaryl groups, and substituted heteroaryl groups. More preferably, $R_7$, $R_8$, $R_{16}$, and $R_{17}$ are independently selected from the group consisting of aryl groups, substituted aryl groups, heteroaryl groups, and substituted heteroaryl groups, with $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups being particularly preferred. More preferably, $R_7$, $R_8$, $R_{16}$, and $R_{17}$ are independently selected from the group consisting of aryl groups and substituted aryl groups, with $C_6$-$C_{10}$ aryl groups and $C_6$-$C_{12}$ substituted aryl groups being particularly preferred. More preferably, $R_7$, $R_8$, $R_{16}$, and $R_{17}$ are independently selected from the group consisting of aryl groups, with $C_6$-$C_{10}$ aryl groups being particularly preferred. In a particularly preferred embodiment, $R_7$, $R_8$, $R_{16}$, and $R_{17}$ are phenyl groups.

In another preferred embodiment, $R_{11}$ and $R_{12}$ are independently selected from the group consisting of haloalkyl groups, aralkyl groups, aryl groups, substituted aryl groups, heteroaryl groups, and substituted heteroaryl groups. More preferably, $R_{11}$ and $R_{12}$ are independently selected from the group consisting of aryl groups, substituted aryl groups, heteroaryl groups, and substituted heteroaryl groups, with $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups being particularly preferred. More preferably, $R_{11}$ and $R_{12}$ are independently selected from the group consisting of aryl groups and substituted aryl groups, with $C_6$-$C_{10}$ aryl groups and $C_6$-$C_{12}$ substituted aryl groups being particularly preferred. More preferably, $R_{11}$ and $R_{12}$ are independently selected from the group consisting of aryl groups, with $C_6$-$C_{10}$ aryl groups being particularly preferred. In a particularly preferred embodiment, $R_{11}$ and $R_{12}$ are phenyl groups.

In a particularly preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups; $R_7$, $R_8$, $R_{16}$, and $R_{17}$ are independently selected from the group consisting of haloalkyl groups, aralkyl groups, aryl groups, substituted aryl groups, heteroaryl groups, and substituted heteroaryl groups; and $R_{11}$ and $R_{12}$ are independently selected from the group consisting of haloalkyl groups, aralkyl groups, aryl groups, substituted aryl groups, heteroaryl groups, and substituted heteroaryl groups. In a more specific embodiment, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups and substituted alkyl groups; $R_7$, $R_8$, $R_{16}$, and $R_{17}$ are independently selected from the group consisting of aryl groups, substituted aryl groups, heteroaryl groups, and substituted heteroaryl groups; and $R_{11}$ and $R_{12}$ are independently selected from the group consisting of aryl groups, substituted aryl groups, heteroaryl groups, and substituted heteroaryl groups. In yet another specific preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of $C_1$-$C_8$ alkyl groups and $C_1$-$C_8$ substituted alkyl groups; $R_7$, $R_8$, $R_{16}$, and $R_{17}$ are independently selected from the group consisting of $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups; and $R_{11}$ and $R_{12}$ are independently selected from the group consisting of $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups. In another specific preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups; $R_7$, $R_8$, $R_{16}$, and $R_{17}$ are independently selected from the group consisting of aryl groups and substituted aryl groups; and $R_{11}$ and $R_{12}$ are independently selected from the group consisting of aryl groups and substituted aryl groups. In another specific preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of $C_1$-$C_8$ alkyl groups; and $R_7$, $R_8$, $R_{16}$, and $R_{17}$ are independently selected from the group consisting of $C_6$-$C_{10}$ aryl groups, and $C_6$-$C_{12}$ substituted aryl groups; and $R_{11}$ and $R_{12}$ are independently selected from the group consisting of $C_6$-$C_{10}$ aryl groups and $C_6$-$C_{12}$ substituted aryl groups. In another specific preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of alkyl groups; $R_7$, $R_8$, $R_{16}$, and $R_{17}$ are independently selected from the group consisting of aryl groups; and $R_{11}$ and $R_{12}$ are independently selected from the group consisting of aryl groups. In another specific preferred embodiment, $R_2$, $R_3$, $R_4$, $R_5$, $R_6$, $R_{13}$, $R_{14}$, $R_{15}$, $R_{18}$, and $R_{19}$ are independently selected from the group consisting of $C_1$-$C_8$ alkyl groups; $R_7$, $R_8$, $R_{16}$, and $R_{17}$ are independently selected from the group consisting of $C_6$-$C_{10}$ aryl groups; and $R_{11}$ and $R_{12}$ are independently selected from the group consisting of $C_6$-$C_{10}$ aryl groups. In yet another specific preferred embodiment, $R_2$, $R_3$, $R_4$, $R_5$, $R_6$, $R_{13}$, $R_{14}$, $R_{15}$, $R_{18}$, and $R_{19}$ are methyl groups; and $R_7$, $R_8$, $R_{16}$, and $R_{17}$ are phenyl groups; and $R_{11}$ and $R_{12}$ are phenyl groups.

The compound conforming to the structure of Formula (X) can be produced by any suitable method. For example, the compound can be produced by reacting a compound conforming to the structure of Formula (I) as described above in which $R_1$ is hydrogen, a compound conforming to the structure of Formula (XA) below

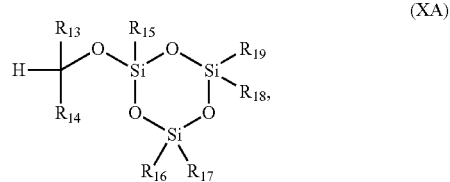

(XA)

and a compound conforming to the structure (XB) below

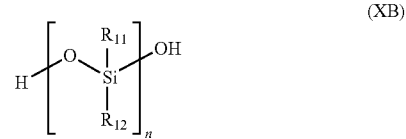

(XB)

in the presence of a suitable Lewis acid catalyst. In the structures of Formulae (XA) and (XB), the groups $R_{11}$, $R_{12}$, $R_{13}$, $R_{14}$, $R_{15}$, $R_{16}$, $R_{17}$, $R_{18}$, and $R_{19}$ are selected from the same groups described above in the discussion of the compound of Formula (X). In such a reaction, the compound conforming to the structure of Formula (I), the compound conforming to the structure of Formula (XA), and the compound conforming to the structure of Formula (XB) are reacted in approximately equimolar amounts. Of course, the compound conforming to the structure of Formula (I) and the compound conforming to the structure of Formula (XA) can be the same compound (i.e., possess the same substituents), in which case about two molar equivalents of the compound conforming to the structure of Formula (I)/(XA) is reacted with about one molar equivalent of the compound conforming to the structure of Formula (XB). Further, if the compound conforming to the structure of Formula (I) and the compound conforming to the structure of Formula (XA) are the same compound, the resulting compound of Formula (X) will be symmetrical. The Lewis acid catalyst used in the reaction preferably is a triphenylborane compound, such as a triphenylborane compound having the formula $B(C_6H_y X_{5-y})_3$ in which y is an integer from 0 to 5, each X is independently selected from the group consisting of F, $OCF_3$, $SCF_3$, R', and OR', and each R' is independently selected from the group consisting of H, $C_1$-$C_{22}$ alkyl, and $C_6$-$C_{22}$ aryl. In a preferred embodiment, the Lewis acid catalyst is tris(pentafluorophenyl)borane.

In a third embodiment, the invention provides a compound conforming to the structure of Formula (XX) below

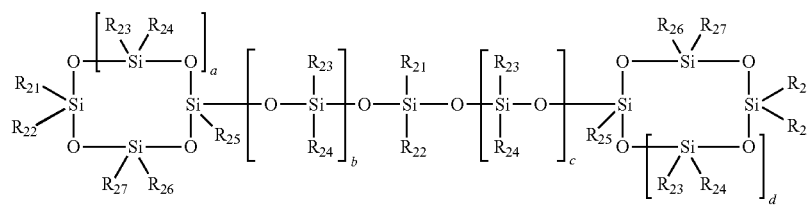

(XX)

In the structure of Formula (XX), the variables a, b, c, and d are integers selected from the group consisting of 0 and 1. The sum of a and b is equal to 1, and the sum of c and d is equal to 1. $R_{21}$, $R_{22}$, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups. At least one of $R_{21}$ and $R_{22}$ is different from each of $R_{23}$, $R_{24}$, $R_{25}$, $R_{26}$, and $R_{27}$.

In a preferred embodiment, at least one of the variables a and d is 0. More preferably, both variables a and d are 0.

In a preferred embodiment, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups. More preferably, $R_{23}$, $R_{24}$, $R_{25}$, $R_{26}$, and $R_{27}$ are independently selected from the group consisting of alkyl groups and substituted alkyl groups, with $C_1$-$C_8$ alkyl groups and $C_1$-$C_8$ substituted alkyl groups being particularly preferred. More preferably, $R_{23}$, $R_{24}$, $R_{25}$, $R_{26}$, and $R_{27}$ are independently selected from the group consisting of alkyl groups, with $C_1$-$C_8$ alkyl groups being particularly preferred. In a particularly preferred embodiment, $R_{23}$, $R_{24}$, $R_{25}$, $R_{26}$, and $R_{27}$ are methyl groups.

In another preferred embodiment, $R_{21}$ and $R_{22}$ are independently selected from the group consisting of haloalkyl groups, aralkyl groups, aryl groups, substituted aryl groups, heteroaryl groups, and substituted heteroaryl groups. More preferably, $R_{21}$ and $R_{22}$ are independently selected from the group consisting of aryl groups, substituted aryl groups, heteroaryl groups, and substituted heteroaryl groups, with $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups being particularly preferred. More preferably, $R_{21}$ and $R_{22}$ are independently selected from the group consisting of aryl groups and substituted aryl groups, with $C_6$-$C_{10}$ aryl groups and $C_6$-$C_{12}$ substituted aryl groups being particularly preferred. More preferably, $R_{21}$ and $R_{22}$ are independently selected from the group consisting of aryl groups, with $C_6$-$C_{10}$ aryl groups being particularly preferred. In a particularly preferred embodiment, $R_{21}$ and $R_{22}$ are phenyl groups.

In a particularly preferred embodiment, the variables a and d are 0, the variables b and c are 1, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, and siloxy groups, and $R_{21}$ and $R_{22}$ are independently selected from the group consisting of haloalkyl groups, aralkyl groups, aryl groups, substituted aryl groups, heteroaryl groups, and substituted heteroaryl groups. In a more specific embodiment, the variables a and d are 0, the variables b and c are 1, $R_{23}$, $R_{24}$, $R_{25}$, $R_{26}$, and $R_{27}$ are independently selected from the group consisting of alkyl groups and substituted alkyl groups, and $R_{21}$ and $R_{22}$ are independently selected from the group consisting of aryl groups, substituted aryl groups, heteroaryl groups, and substituted heteroaryl groups. In yet another specific preferred embodiment, the variables a and d are 0, the variables b and c are 1, $R_{23}$, $R_{24}$, $R_{25}$, $R_{26}$, and $R_{27}$ are independently selected from the group consisting of $C_1$-$C_8$ alkyl groups and $C_1$-$C_8$ substituted alkyl groups, and $R_{21}$ and $R_{22}$ are independently selected from the group consisting of $C_6$-$C_{10}$ aryl groups, $C_6$-$C_{12}$ substituted aryl groups, $C_4$-$C_{10}$ heteroaryl groups, and $C_4$-$C_{12}$ substituted heteroaryl groups. In another specific preferred embodiment, the variables a and d are 0, the variables b and c are 1, $R_{23}$, $R_{24}$, $R_{25}$, $R_{26}$, and $R_{27}$ are independently selected from the group consisting of alkyl groups, and $R_{21}$ and $R_{22}$ are independently selected from the group consisting of aryl groups and substituted aryl groups. In another specific preferred embodiment, the variables a and d are 0, the variables b and c are 1, $R_{23}$, $R_{24}$, $R_{25}$, $R_{26}$, and $R_{27}$ are independently selected from the group consisting of $C_1$-$C_8$ alkyl groups, and $R_{21}$ and $R_{22}$ are independently selected from the group consisting of $C_6$-$C_{10}$ aryl groups and $C_6$-$C_{12}$ substituted aryl groups. In another specific preferred embodiment, the variables a and d are 0, the variables b and c are 1, $R_{23}$, $R_{24}$, $R_{25}$, $R_{26}$, and $R_{27}$ are independently selected from the group consisting of alkyl groups, and $R_{21}$ and $R_{22}$ are independently selected from the group consisting of aryl groups. In another specific preferred embodiment, the variables a and d are 0, the variables b and c are 1, $R_{23}$, $R_{24}$, $R_{25}$, $R_{26}$, and $R_{27}$ are independently selected from the group consisting of $C_1$-$C_8$ alkyl groups, and $R_{21}$ and $R_{22}$ are independently selected from the group consisting of $C_6$-$C_{10}$ aryl groups. In yet another specific preferred embodiment, the variables a and d are 0, the variables b and c are 1, $R_{23}$, $R_{24}$, $R_{25}$, $R_{26}$, and $R_{27}$ are methyl groups, and $R_{21}$ and $R_{22}$ are phenyl groups.

The compound conforming to the structure of Formula (XX) can be produced by any suitable method. For example, the compound can be produced by reacting a hydrosiloxane compound conforming to the structure of Formula (XXA) below

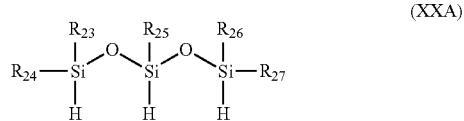

(XXA)

with a compound conforming to the structure of Formula (XXB) below

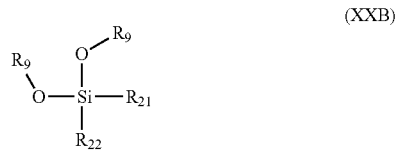

(XXB)

in the presence of a suitable Lewis acid catalyst. In the structures of Formulae (X×A) and (X×B), $R_{21}$, $R_{22}$, $R_{23}$, $R_{24}$, $R_{25}$, $R_{26}$, and $R_{27}$ are selected from the same groups recited above for the structure of Formula (XX). Each $R_9$ is independently selected from the group consisting of hydrogen, alkyl groups, and substituted alkyl groups. Preferably, each $R_9$ is hydrogen. The Lewis acid catalyst used in the reaction preferably is a triphenylborane compound, such as a triphenylborane compound having the formula $B(C_6H_y X_{5-y})_3$ in which y is an integer from 0 to 5, each X is independently selected from the group consisting of F, $OCF_3$, $SCF_3$, R', and OR', and each R' is independently selected from the group consisting of H, $C_1$-$C_{22}$ alkyl, and $C_6$-$C_{22}$ aryl. In a preferred embodiment, the Lewis acid catalyst is tris(pentafluorophenyl)borane. In the above-described reaction, the compound conforming to the structure of Formula (XXA) and the compound conforming to the structure of Formula (XXB) preferably are reacted in a ratio of about three molar equivalents of the compound of Formula (XXB) to two molar equivalents of the compound of Formula (XXA). In the reaction, the compound of Formula (XXB) can react with adjacent silicon atoms in the compound conforming to the structure of Formula (XXA), which reaction will yield a cyclotrisiloxane ring. More specifically, in the context of the structure of Formula (XX), such a reaction will yield a compound in which one of the variables a and d is 0 and the value for the corresponding variable b or c is 1. During the reaction, the compound of Formula (XXB) can also react with the terminal silicon atoms in the compound conforming to the structure of Formula (XXA), which reaction will yield a cyclotetrasiloxane ring. More specifically, in the context of the structure of Formula (XX), such a reaction will yield a compound in which one of the variables a and d is 1 and the value for the corresponding variable b or c is 0. The compound of Formula (XXB) can also react with silicon atoms on different molecules of the compound conforming to the structure of Formula (XXA), which reaction will produce a link between separate molecules of the compound conforming to the structure of Formula (XXA) or a link between cyclic siloxane moieties as is illustrated in the structure of Formula (XX).

In a fourth embodiment, the invention provides a composition comprising (a) a first siloxane compound selected from the group consisting of compounds conforming to the structure of Formula (X) and compounds conforming to the structure of Formula (XX) and (b) a second siloxane compound. The first siloxane compound can be selected from any of the compounds conforming to the structures of Formulae (X) and (XX) described above. The second siloxane compound can be any suitable siloxane compound. In a preferred embodiment, the second siloxane compound comprises a plurality of siloxane repeating units wherein about 10 mol. % or more of the siloxane repeating units are cyclotrisiloxane repeating units and the cyclotrisiloxane repeating units are independently selected from the group consisting of cyclotrisiloxane repeating units conforming to the structure of Formula (XL) below:

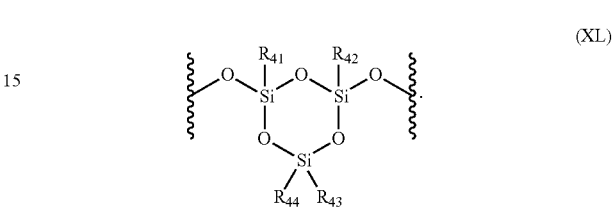

(XL)

In the structure of Formula (XL), $R_{41}$ and $R_{42}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. $R_{43}$ and $R_{44}$ are independently selected from the group consisting of haloalkyl groups, aralkyl groups, aryl groups, substituted aryl groups, heteroaryl groups, and substituted heteroaryl groups.

In a preferred embodiment of the composition of this fourth embodiment, the first siloxane compound is a compound conforming to the structure of Formula (XX). In a specific preferred embodiment of such a composition, the variables a and d are 0, the variables b and c are 1, $R_{23}$, $R_{24}$, $R_{25}$, $R_{26}$, and $R_{27}$ are independently selected from the group consisting of $C_1$-$C_8$ alkyl groups, and $R_{21}$ and $R_{22}$ are independently selected from the group consisting of $C_6$-$C_{10}$ aryl groups. In another specific preferred embodiment, the variables a and d are 0, the variables b and c are 1, $R_{23}$, $R_{24}$, $R_{25}$, $R_{26}$, and $R_{27}$ are methyl groups, and $R_{21}$ and $R_{22}$ are phenyl groups.

The second siloxane compound can be any suitable siloxane compound possessing the amount of cyclotrisiloxane moieties recited above. Suitable siloxane compounds and methods for making the same are described, for example, in U.S. patent application Ser. No. 14/244,193 filed on Apr. 3, 2014, which application published as U.S. Patent Application Publication No. US 2014/0309448 A1 on Oct. 16, 2014 and is hereby incorporated by reference for its disclosure of such siloxane compounds and processes for making the same. In the structure of Formula (XL) and the structures that follow, the partial bonds (i.e., the bonds truncated by the wavy line) represent bonds to adjacent moieties or repeating units within the second siloxane compound. In a preferred embodiment, $R_{41}$ and $R_{42}$ are independently selected from the group consisting of alkyl groups and substituted alkyl groups, and $R_{43}$ and $R_{44}$ are independently selected from the group consisting of haloalkyl groups, aralkyl groups, and aryl groups. In a more specific preferred embodiment, $R_{41}$ and $R_{42}$ are independently selected from the group consisting of $C_1$-$C_8$ alkyl groups and $C_1$-$C_8$ substituted alkyl groups, and $R_{43}$ and $R_{44}$ are independently selected from the group consisting of $C_1$-$C_8$ haloalkyl groups, $C_6$-$C_{10}$ aryl groups, and $C_7$-$C_{31}$ aralkyl groups. In another preferred embodiment, $R_{41}$ and $R_{42}$ are independently selected from the group consisting of $C_1$-$C_8$ alkyl groups, and $R_{43}$ and $R_{44}$ are independently selected from the group consisting of $C_6$-$C_{10}$ aryl groups. In another preferred embodiment, $R_{41}$ and $R_{42}$ are methyl groups, and $R_{43}$ and $R_{44}$ are phenyl groups.

The second siloxane compound can comprise any suitable amount of siloxane repeating units conforming to the structure of Formula (XL). Preferably, about 10 mol. % or more of the siloxane repeating units in the second siloxane compound conform to the structure of Formula (XL). More preferably, about 15 mol. % or more, about 20 mol. % or more, about 25 mol. % or more, about 30 mol. % or more, about 35 mol. % or more, about 40 mol. % or more, about 45 mol. % or more, about 50 mol. % or more, about 55 mol. % or more, about 60 mol. % or more, about 65 mol. % or more, about 70 mol. % or more, about 75 mol. % or more, about 80 mol. % or more, about 85 mol. % or more, or about 90 mol. % or more of the siloxane repeating units in the second siloxane compound conform to the structure of Formula (XL).

The cyclotrisiloxane repeating units present in the second siloxane compound possess the same basic structure (i.e., a structure conforming to Formula (XL)), but all of the repeating units are not necessarily substituted with the same groups. In other words, the siloxane compound can contain cyclotrisiloxane repeating units that differ in the selection of the $R_{41}$, $R_{42}$, $R_{43}$, and $R_{44}$ substituents.

The second siloxane compound can comprise siloxane units in addition to those conforming to the structure of Formula (XL). For example, in a preferred embodiment, the siloxane compound can comprise one or more siloxane moieties conforming to the structure of Formula (L) below:

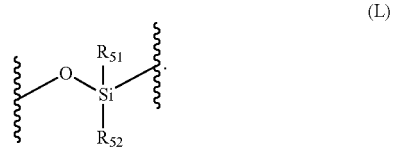

(L)

In the structure of Formula (L), $R_{51}$ and $R_{52}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups. More preferably, $R_{51}$ and $R_{52}$ are independently selected from the group consisting of $C_1$-$C_{30}$ alkyl groups (e.g., $C_1$-$C_8$ alkyl groups), $C_2$-$C_{30}$ alkenyl groups (e.g., $C_2$-$C_8$ alkenyl groups), $C_1$-$C_{30}$ haloalkyl groups (e.g., $C_1$-$C_8$ haloalkyl groups), $C_6$-$C_{30}$ aryl groups (e.g., $C_6$-$C_{10}$ aryl groups), $C_7$-$C_{31}$ aralkyl groups, $C_3$-$C_9$ trialkylsiloxy groups, $C_8$-$C_{26}$ aryldialkylsiloxy groups, $C_{13}$-$C_{28}$ alkyldiarylsiloxy groups, and $C_{18}$-$C_{30}$ triarylsiloxy groups. More preferably, $R_{51}$ and $R_{52}$ are independently selected from the group consisting of $C_1$-$C_8$ alkyl groups, $C_1$-$C_8$ haloalkyl groups, $C_6$-$C_{10}$ aryl groups, and $C_7$-$C_{31}$ aralkyl groups. Most preferably, $R_{51}$ and $R_{52}$ are independently selected from the group consisting of $C_1$-$C_8$ alkyl groups, with methyl groups being particularly preferred.

The structures drawn above only represent repeating units within the second siloxane compound. The second siloxane compound further comprises terminating groups. These terminating groups can be any suitable terminating group for a siloxane compound. In a preferred embodiment, the second siloxane compound further comprises silyl terminating groups. Suitable silyl terminating groups include, but are not limited to, trialkylsilyl groups, such as trimethylsilyl groups.

The second siloxane compound preferably is an oligomeric or polymeric siloxane compound comprising multiple siloxane moieties including the cyclotrisiloxane moieties described above. Preferably, the second siloxane compound has a number average molar mass of about 1,000 g/mol or more. The number average molar mass ($M_n$) of the second siloxane compound is more preferably about 2,000 g/mol or more, about 3,000 g/mol or more, or about 4,000 g/mol or more. Preferably, the second siloxane compound has a mass average molar mass (Mw) that is at least 50% greater than the number average molar mass of the compound. In a series of preferred embodiments, the second siloxane compound has a mass average molar mass of about 8,000 g/mol or more, about 10,000 g/mol or more, about 11,000 g/mol or more, or about 12,000 g/mol or more.

The composition of this fourth embodiment of the invention can comprise other siloxane compounds in addition to the compound conforming to the structure of Formula (XX) and the second siloxane compound. In one such embodiment, the composition further comprises a third siloxane compound conforming to the structure of Formula (LX) below

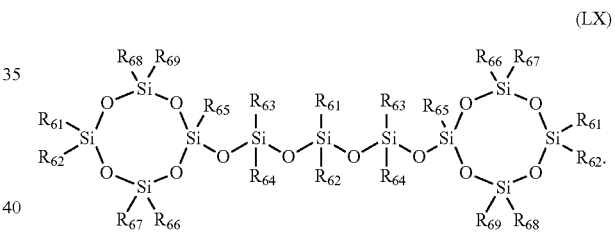

(LX)

In the structure of Formula (LX), $R_{61}$ and $R_{62}$ are independently selected from the group consisting of haloalkyl groups, aralkyl groups, aryl groups, substituted aryl groups, heteroaryl groups, and substituted heteroaryl groups. $R_{63}$, $R_{64}$, $R_{65}$, $R_{66}$, $R_{67}$, $R_{68}$, and $R_{69}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups.

Siloxane compounds conforming to the structure of Formula (LX) are described, for example, in U.S. patent application Ser. No. 14/244,264 filed on Apr. 3, 2014, which application published as U.S. Patent Application Publication No. US 2014/0309450 A1 on Oct. 16, 2014 and is hereby incorporated by reference for its disclosure of such siloxane compounds and processes for making the same. In a preferred embodiment, $R_{63}$, $R_{64}$, $R_{66}$, $R_{67}$, $R_{68}$, and $R_{69}$ are independently selected from the group consisting of alkyl groups and substituted alkyl groups, and $R_{61}$, $R_{62}$, and $R_{65}$ are independently selected from the group consisting of haloalkyl groups, aralkyl groups, and aryl groups. In a more specific preferred embodiment, $R_{63}$, $R_{64}$, $R_{66}$, $R_{67}$, $R_{68}$, and $R_{69}$ are independently selected from the group consisting of $C_1$-$C_8$ alkyl groups and $C_1$-$C_8$ substituted alkyl groups, and $R_{61}$, $R_{62}$, and $R_{65}$ are independently selected from the group consisting of $C_1$-$C_8$ haloalkyl groups, $C_6$-$C_{10}$ aryl groups, and $C_7$-$C_{31}$ aralkyl groups. In another preferred embodiment, $R_{63}$, $R_{64}$, $R_{66}$, $R_{67}$, $R_{68}$, and $R_{69}$ are independently selected from the group consisting of $C_1$-$C_8$ alkyl groups, and $R_{61}$, $R_{62}$, and $R_{65}$ are independently selected from the group consisting of $C_6$-$C_{10}$ aryl groups. In another preferred embodiment, $R_{63}$, $R_{64}$, $R_{66}$, $R_{67}$, $R_{68}$, and $R_{69}$ are methyl groups, and $R_{61}$, $R_{62}$, and $R_{65}$ are phenyl groups.

The composition of this fourth embodiment of the invention can be used to produce a cross-linked silicone polymer. For example, the composition, which contains a siloxane compound conforming to the structure of Formula (XX) and a second siloxane compound as described above, can be combined with a ring-opening catalyst. When the composition is combined with a ring-opening catalyst, the catalyst opens at least a portion of the cyclotrisiloxane rings on the compound conforming to the structure of Formula (XX) or at least a portion of the cyclotrisiloxane moieties in the second siloxane compound. These ring-opened moieties on the compounds in the composition then react with other molecules in the composition to produce cross-links between different molecules in the composition, which ultimately results in a cross-linked silicone polymer. When the composition comprises a third siloxane compound conforming to the structure of Formula (LX), the ring-opening catalyst can also open at least a portion of the cyclotetrasiloxane moieties in the third siloxane compound, and such ring-opened moieties can react with other molecules in the composition to produce a cross-linked silicone polymer as described above.

The ring-opening catalyst can be any suitable compound that is capable of catalyzing the opening of the cyclosiloxane moieties within the compounds included in the composition, such as the first siloxane compound. Suitable catalysts are described, for example, in Chapter 1 of the book *Silicon-Containing Polymers: The Science and Technology of Their Synthesis and Applications* (James et al., Dordrecht: Kluwer Academic Publishers, 2000), in Chapter 3 of the book *Handbook of Ring-Opening Polymerization* (Dubois et al., Weinheim: WILEY-VCH Verlag GmbH & Co. KGaA, 2009), in U.S. Patent Application Publication No. 2008/0097064 A1 (Blanc-Magnard et al.), by Jaroentomeechai et al. in *Inorg. Chem.* 2012, 51, 12266-72, and by Gilbert et al. in *Journal of Polymer Science* 1959, XL, 35-58. One suitable class of ring-opening catalysts is compounds comprising one or more silanolate or siloxanolate moieties. In a preferred embodiment, the ring-opening catalyst can be selected from the group consisting of siloxanolate salts (e.g., tetramethylammonium siloxanolate), dialkarylsilanolate salts (e.g., sodium dimethylphenylsilanolate), ammonium hydroxides (e.g., tetraalkylammonium hydroxides), and phosphonium hydroxides (e.g., tetraalkylphosphonium hydroxides). More preferably, the ring-opening catalyst is selected from the group consisting of ammonium hydroxides and phosphonium hydroxides, such as tetrabutylphosphonium hydroxide.

The compound conforming to the structure of Formula (XX), the second siloxane, and the third siloxane compound (if present) can be present in the composition in any suitable relative amounts. For example, the compound conforming to the structure of Formula (XX) and the second siloxane compound can be present in a ratio of about 1 part or more of the compound conforming to the structure of Formula (XX) to about 1 part of the second siloxane compound. Preferably, the compound conforming to the structure of Formula (XX) and the second siloxane compound are present in a ratio of about 2 parts or more (e.g., about 3 parts) of the compound conforming to the structure of Formula (XX) to about 1 part of the second siloxane compound. In those compositions comprising the third siloxane compound, the third siloxane compound can be present in the composition in a ratio of about 1 part or more of the compound conforming to the structure of Formula (XX) to about 1 part of the third siloxane compound. More preferably, the third siloxane compound can be present in the composition in a ratio of about 2 parts or more, about 3 parts or more, or about 4 parts or more of the compound conforming to the structure of Formula (XX) to about 1 part of the third siloxane compound.

The cross-linked siloxane polymer produced from the composition as described above can be used in many applications. For example, the cross-linked siloxane polymer can be used as an encapsulant for light emitting diodes (LEDs). Because the cross-linked silicone polymer can be made from raw materials containing relatively large amounts of groups that increase the refractive index of the polymer (e.g., haloalkyl groups, aralkyl groups, aryl groups, substituted aryl groups, heteroaryl groups, and substituted heteroaryl groups), it is believed that the cross-linked silicone polymer can be particularly effective as an encapsulant for high intensity LEDs. In such applications, an encapsulant having a higher refractive index provides a progressive transition from the relatively high refractive index of the semiconductor crystal (where the light is produced on the LED) to the air surrounding the LED. The relatively large difference between the refractive index of the semiconductor crystal and the surrounding air leads to internal reflection of light within the LED's semiconductor crystal. These internal reflections reduce the amount of light that escapes from the semiconductor crystal and is emitted by the LED. By providing a medium with an intermediate refractive index (i.e., a refractive index between the high refractive index of the semiconductor crystal and the refractive index of air), the encapsulant material (i.e., the cross-linked silicone polymer) can reduce the amount of light that is internally reflected back into the semiconductor crystal, thereby increasing the amount of light emitted by the LED. This use of similar cross-linked silicone polymers is described, for example, in U.S. patent application Ser. No. 14/244,236 filed on Apr. 3, 2014, which application published as U.S. Patent Application Publication No. 2014/0306259 on Oct. 16, 2014 and is hereby incorporated by reference for its disclosure of methods of making such encapsulant materials and uses for the same.

The following examples further illustrate the subject matter described above but, of course, should not be construed as in any way limiting the scope thereof.

Example 1

This example demonstrates the synthesis of a compound conforming to the structure Formula (I).

Approximately 100 g of heptane and approximately 0.06 g tris(pentafluorophenyl)borane were added under nitrogen to a 500 ml three neck flask equipped with a magnetic stirring bar. The temperature of the solution was raised to approximately 95° C. with constant stirring. Using two separate syringes, approximately 19.00 g diphenyldimethoxy silane and approximately 15.5 g of 1,1,3,5,5-pentamethyltrisiloxane were slowly added at the same time over the course of 3 hours while maintaining the temperature at approximately 95° C. under vigorous stirring. The amounts for both the components were allowed to react slowly at an approximately 1:1 molar ratio. After the addition was complete, another 2 g of heptane was used to rinse all of the remaining contents pf the syringes into the reaction mixture. The reaction mixture was then stirred for one additional hour at 95° C. The resulting product was cooled to ambient temperature. Approximately 1 g of carbon black and approximately 0.5 g of magnesium oxide were then added and the mixture was stirred for approximately 1 hour. The resulting mixture was then filtered to recover the liquid product and analyzed using $^{29}$Si NMR and liquid chromatography-mass spectrometry (LCMS). The LCMS results showed an approximately 22.4 min peak and approximately 410 molecular weight peak. The $^{29}$Si NMR (ppm, CDCl$_3$) showed δ −3, −16, −35, and −55 ppm peaks. The refractive index of the product was approximately 1.515, and the product was a free-flowing liquid.

Example 2

This example demonstrates the synthesis of a compound conforming to the structure Formula (I).

Approximately 50 g of heptane, approximately 0.02 g of tris(pentafluorophenyl)borane, and approximately 10 g of 1,1,3,5,5-pentamethyltrisiloxane were added under nitrogen to a 250 ml three neck flask equipped with a magnetic stirring bar. The temperature of the mixture was raised to a temperature of approximately 95° C. with constant stirring. Using a syringe, approximately 12.57 g of diphenyldimethoxy silane was slowly added over a period of approximately 24 hours while maintaining the temperature at approximately 95° C. under vigorous stirring. After the addition was complete, approximately 2 g of heptane was used to rinse the remaining contents of the syringe into the reaction mixture. The reaction mixture was then stirred for one additional hour at 95° C. and cooled to ambient temperature. Approximately 0.6 g of carbon black and approximately 0.4 g of magnesium oxide were added to the reaction mixture and the resulting mixture was stirred for 1 hour. The mixture was then filtered to recover the liquid product and analyzed using $^{29}$Si NMR and liquid chromatography-mass spectrometry (LCMS). The LCMS results showed an approximately 22.4 min peak and approximately 410 molecular weight peak. The $^{29}$Si NMR (ppm, CDCl$_3$) showed δ −3, −16, −36, and −56 ppm peaks. The refractive index of the product was approximately 1.515, and the product was a free-flowing liquid.

Example 3

This example demonstrates the preparation of a siloxane compound conforming to the structure of Formula (XX).

Approximately 185 ml of xylene and approximately 27.3 g diphenylsilanediol (126 mmol) were added to a 500 ml round bottom flask equipped with a heating mantle, magnetic stirrer, temperature controller, condenser, and nitrogen bubbler. The contents of the flask were heated to a temperature of approximately 30° C. and stirred to dissolve or suspend the diphenylsilanediol. In a separate vessel, approximately 0.2 g of tris(pentafluorophenyl)borane was dissolved in approximately 4 g xylene to yield an approximately 5% solution of tris(pentafluorophenyl)borane. Approximately 0.6 ml of the 5% solution of tris(pentafluorophenyl)borane was added to the round bottom flask. In another separate vessel, approximately 15.5 g of 1,1,3,5,5-pentamethyltrisiloxane (80 mmol) was dissolved in approximately 45 ml of xylene. The resulting solution of 1,1,3,5,5-pentamethyltrisiloxane was placed in an additional funnel connected to the 500 ml round bottom flask. Approximately 5 ml of the 1,1,3,5,5-pentamethyltrisiloxane solution was then added to the round bottom flask. The nitrogen bubbler was monitored for hydrogen gas evolution. When hydrogen gas evolution was detected, the remainder of the 1,1,3,5,5-pentamethyltrisiloxane solution was then added to the round bottom flask over a period of approximately 2 hours while stirring the contents of the flask and maintaining a temperature of approximately 30-40° C. Once the addition of the 1,1,3,5,5-pentamethyltrisiloxane solution was completed, the contents of the flask were heated to a temperature of approximately 60° C. and held at this temperature for approximately 1 hour. A sample was then taken and submitted for FTIR analysis to determine if all of the Si—H had reacted. The contents of the flask were maintained at a temperature of 60° C. while the FTIR analysis was completed. Once the absence of Si—H was confirmed, approximately 0.6 g of magnesium oxide and approximately 3 g of activated carbon were added to the round bottom flask and the mixture was stirred at room temperature for approximately 30 minutes. The contents of the round bottom flask were filtered and placed into a 1 liter round bottom flask. The solvent was removed under reduced pressure using a rotary evaporator at a temperature of approximately 95° C. The process yielded approximately 36.8 g of product having a refractive index of approximately 1.5244 and a viscosity of approximately 2675 cP.

Example 4

This example demonstrates the synthesis of a composition according to the invention and the use of that composition in the production of a cross-linked silicone polymer.

Approximately one part of a polymeric siloxane compound comprising a plurality of cyclotrisiloxane moieties conforming to the structure of Formula (XL) was combined with approximately four parts of a compound conforming to the structure of Formula (XX) to form a composition designated as "Part 4A." In the compound comprising the cyclotrisiloxane moieties conforming to the structure of Formula (XL), $R_{41}$ and $R_{42}$ were methyl groups, and $R_{43}$ and $R_{44}$ were phenyl groups. In the compound conforming to the structure of Formula (XX), the variables a and d were 0, the variables b and c were 1, $R_{23}$, $R_{24}$, $R_{25}$, $R_{26}$, and $R_{27}$ were methyl groups, and $R_{21}$ and $R_{22}$ were phenyl groups.

Approximately 20 parts of Part 4A was combined with one part of a catalyst composition designated as "Part 4B" and the resulting mixture was thoroughly mixed. The Part 4B composition contained approximately 1 wt. % tetrabutylphosphonium hydroxide in PM-125 phenylmethyl silicone fluid (Clearco Products). The mixture of Part 4A and Part 4B exhibited a viscosity of approximately 4,000 cPs. The mixture was then heated at a temperature of approximately 85° C. for approximately 1 hour and heated for an additional hour at a temperature of approximately 150° C.

After curing, the resulting product was a transparent silicone elastomer. The elastomer exhibited a durometer hardness of Shore A 65. The silicone elastomer exhibited an optical transparency of approximately 98.3% as measured at a wavelength of 450 nm in a 1 mm thick sample.

Example 5

This example demonstrates the synthesis of a composition according to the invention and the use of that composition in the production of a cross-linked silicone polymer.

Approximately one part of a polymeric siloxane compound comprising a plurality of cyclotrisiloxane moieties conforming to the structure of Formula (XL) was combined with approximately three parts of a compound conforming to the structure of Formula (XX), approximately one part of a compound conforming to the structure of Formula (LX), and approximately 500 ppm of a defoamer to form a composition designated as "Part 5A." In the compound comprising the cyclotrisiloxane moieties conforming to the structure of Formula (XL), $R_{41}$ and $R_{42}$ were methyl groups, and $R_{43}$ and $R_{44}$ were phenyl groups. In the compound conforming to the structure of Formula (XX), the variables a and d were 0, the variables b and c were 1, $R_{23}$, $R_{24}$, $R_{25}$, $R_{26}$, and $R_{27}$ were methyl groups, and $R_{21}$ and $R_{22}$ were phenyl groups. In the compound conforming to the structure of Formula (LX), $R_{63}$, $R_{64}$, $R_{65}$, $R_{66}$, $R_{67}$, $R_{68}$, and $R_{69}$ were methyl groups, and $R_{61}$ and $R_{62}$ were phenyl groups Approximately 20 parts of Part 5A was combined with one part of a catalyst composition designated as "Part 5B" and the resulting mixture was thoroughly mixed. The Part 5B composition contained approximately 1 wt. % tetrabutylphosphonium hydroxide in PM-125 phenylmethyl silicone fluid (Clearco Products). The mixture of Part 5A and Part 5B exhibited a viscosity of approximately 3,820 cPs, a pot life of approximately 6.5 hours, and a gel point of approximately 81.8° C. The mixture was then heated at a temperature of approximately 85° C. for approximately 1 hour and heated for an additional hour at a temperature of approximately 150° C.

After curing, the resulting product was a transparent silicone elastomer. The elastomer exhibited a durometer hardness of Shore A 64. The silicone elastomer exhibited an optical transparency of approximately 98% as measured at a wavelength of 450 nm in a 1 mm thick sample. The silicone elastomer exhibited a refractive index of approximately 1.52.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A compound conforming to the structure of Formula (I) below

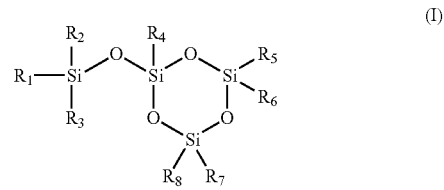

wherein $R_1$ is —$OR_9$; $R_9$ is selected from the group consisting of alkyl groups and substituted alkyl groups; $R_2$, $R_3$, $R_4$, $R_5$, $R_6$, $R_7$, and $R_8$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$.

2. The compound of claim 1, wherein $R_7$ and $R_8$ are independently selected from the group consisting of haloalkyl groups, aralkyl groups, aryl groups, substituted aryl groups, heteroaryl groups, and substituted heteroaryl groups.

3. The compound of claim 2, wherein $R_7$ and $R_8$ are independently selected from the group consisting of aryl groups, substituted aryl groups, heteroaryl groups, and substituted heteroaryl groups.

4. The compound of claim 3, wherein $R_7$ and $R_8$ are phenyl groups.

5. The compound of claim 1, wherein $R_2$, $R_3$, $R_4$, $R_5$, and $R_6$ are independently selected from the group consisting of alkyl groups and substituted alkyl groups.

6. The compound of claim 5, wherein $R_2$, $R_3$, $R_4$, $R_5$, and $R_6$ are methyl groups.

7. The compound of claim 1, wherein $R_9$ is a methyl group.

8. A compound conforming to the structure of Formula (X) below

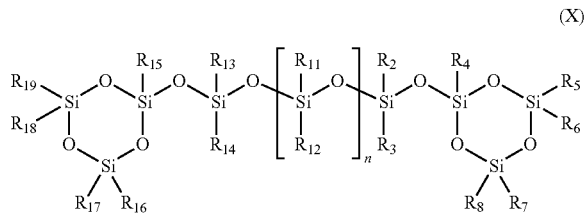

(X)

wherein $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, and $R_{19}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$ and at least one of $R_{16}$ and $R_{17}$ is different from each of $R_{13}$, $R_{14}$, $R_{15}$, $R_{18}$, and $R_{19}$; and n is selected from the group consisting of integers equal to or greater than 1.

9. The compound of claim 8, wherein $R_7$, $R_8$, $R_{16}$, and $R_{17}$ are independently selected from the group consisting of haloalkyl groups, aralkyl groups, aryl groups, substituted aryl groups, heteroaryl groups, and substituted heteroaryl groups.

10. The compound of claim 9, wherein $R_7$, $R_8$, $R_{16}$, and $R_{17}$ are independently selected from the group consisting of aryl groups, substituted aryl groups, heteroaryl groups, and substituted heteroaryl groups.

11. The compound of claim 10, wherein $R_7$, $R_8$, $R_{16}$, and $R_{17}$ are phenyl groups.

12. The compound of claim 8, wherein $R_2$, $R_3$, $R_4$, $R_5$, $R_6$, $R_{13}$, $R_{14}$, $R_{15}$, $R_{18}$, and $R_{19}$ are independently selected from the group consisting of alkyl groups and substituted alkyl groups.

13. The compound of claim 12, wherein $R_2$, $R_3$, $R_4$, $R_5$, $R_6$, $R_{13}$, $R_{14}$, $R_{15}$, $R_{18}$, and $R_{19}$ are methyl groups.

14. The compound of claim 8, wherein $R_{11}$ and $R_{12}$ are independently selected from the group consisting of haloalkyl groups, aralkyl groups, aryl groups, substituted aryl groups, heteroaryl groups, and substituted heteroaryl groups.

15. The compound of claim 14, wherein $R_{11}$ and $R_{12}$ are independently selected from the group consisting of aryl groups, substituted aryl groups, heteroaryl groups, and substituted heteroaryl groups.

16. The compound of claim 15, wherein $R_{11}$ and $R_{12}$ are phenyl groups.

17. A compound conforming to the structure of Formula (XX) below wherein a, b, c, and d are integers selected from the group consisting of 0 and 1; the sum of a and b is equal to 1; the sum of c and d is equal to 1; and $R_{21}$, $R_{22}$, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_{21}$ and $R_{22}$ is different from each of $R_{23}$, $R_{24}$, $R_{25}$, $R_{26}$, and $R_{27}$.

18. The compound of claim 17, wherein $R_{21}$ and $R_{22}$ are independently selected from the group consisting of haloalkyl groups, aralkyl groups, aryl groups, substituted aryl groups, heteroaryl groups, and substituted heteroaryl groups.

19. The compound of claim 18, wherein $R_{21}$ and $R_{22}$ are independently selected from the group consisting of aryl groups, substituted aryl groups, heteroaryl groups, and substituted heteroaryl groups.

20. The compound of claim 19, wherein $R_{21}$ and $R_{22}$ are aryl groups.

21. The compound of claim 20, wherein $R_{21}$ and $R_{22}$ are phenyl groups.

22. The compound of claim 17, wherein $R_{23}$, $R_{24}$, $R_{25}$, $R_{26}$, and $R_{27}$ are independently selected from the group consisting of alkyl groups and substituted alkyl groups.

23. The compound of claim 22, wherein $R_{23}$, $R_{24}$, $R_{25}$, $R_{26}$, and $R_{27}$ are independently selected from the group consisting of alkyl groups.

24. The compound of claim 23, wherein $R_{23}$, $R_{24}$, $R_{25}$, $R_{26}$, and $R_{27}$ are methyl groups.

25. A composition comprising:
(a) a first siloxane compound selected from the group consisting of compounds conforming to the structure of Formula (X) and compounds conforming to the structure of Formula (XX), wherein the structure of Formula (X) is

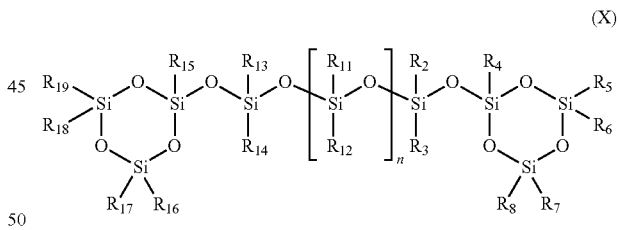

(X)

wherein $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, and $R_{19}$ are independently selected from the group consisting of alkyl groups, substituted alkyl groups, cycloalkyl groups, substituted cycloalkyl groups, alkenyl

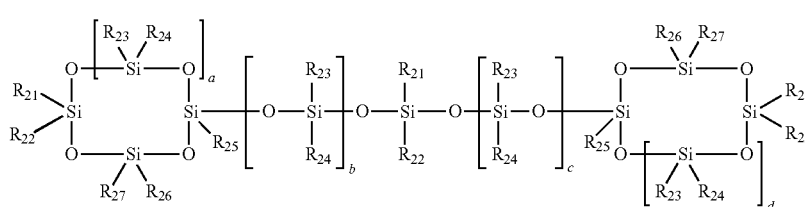

(XX)

groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_7$ and $R_8$ is different from each of $R_2$, $R_3$, $R_4$, $R_5$, and $R_6$ and at least one of $R_{16}$ and $R_{17}$ is different from each of $R_{13}$, $R_{14}$, $R_{15}$, $R_{18}$, and $R_{19}$; and n is selected from the group consisting of integers equal to or greater than 1; and the structure of Formula (XX) is

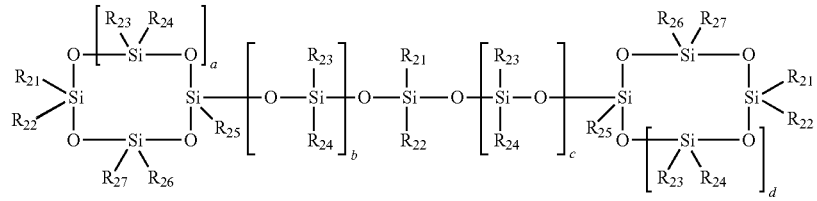

(XX)

wherein a, b, c, and d are integers selected from the group consisting of 0 and 1; the sum of a and b is equal to 1; the sum of c and d is equal to 1; and $R_{21}$, $R_{22}$, $R_{23}$, $R_{24}$, $R_{25}$, $R_{26}$, and $R_{27}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups, and siloxy groups, provided at least one of $R_{21}$ and $R_{22}$ is different from each of $R_{23}$, $R_{24}$, $R_{25}$, $R_{26}$, and $R_{27}$; and (b) a second siloxane compound, wherein the second siloxane compound comprises a plurality of siloxane repeating units, about 10 mol. % or more of the siloxane repeating units are cyclotrisiloxane repeating units, the cyclotrisiloxane repeating units are independently selected from the group consisting of cyclotrisiloxane repeating units conforming to the structure of Formula (XL) below:

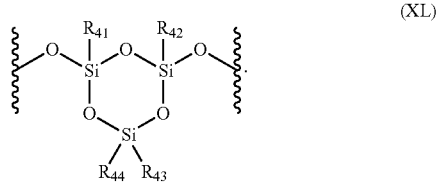

(XL)

wherein $R_{41}$ and $R_{42}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_{43}$ and $R_{44}$ are independently selected from the group consisting of haloalkyl groups, aralkyl groups, aryl groups, substituted aryl groups, heteroaryl groups, and substituted heteroaryl groups.

26. The composition of claim 25, wherein the first siloxane compound is a compound conforming to the structure of Formula (XX), and $R_{21}$ and $R_{22}$ are independently selected from the group consisting of aryl groups, substituted aryl groups, heteroaryl groups, and substituted heteroaryl groups.

27. The composition of claim 26, wherein $R_{21}$ and $R_{22}$ are phenyl groups.

28. The composition of claim 25, wherein the first siloxane compound is a compound conforming to the structure of Formula (XX), and $R_{23}$, $R_{24}$, $R_{25}$, $R_{26}$, and $R_{27}$ are independently selected from the group consisting of alkyl groups and substituted alkyl groups.

29. The composition of claim 28, wherein $R_{23}$, $R_{24}$, $R_{25}$, $R_{26}$, and $R_{27}$ are methyl groups.

30. The composition of claim 25, wherein $R_{41}$ and $R_{42}$ are independently selected from the group consisting of alkyl groups.

31. The composition of claim 30, wherein $R_{41}$ and $R_{42}$ are methyl groups.

32. The composition of claim 25, wherein $R_{43}$ and $R_{44}$ are independently selected from the group consisting of aryl groups.

33. The composition of claim 32, wherein $R_{43}$ and $R_{44}$ are phenyl groups.

34. The composition of claim 25, wherein the composition further comprises a third siloxane compound conforming to the structure of Formula (LX) below

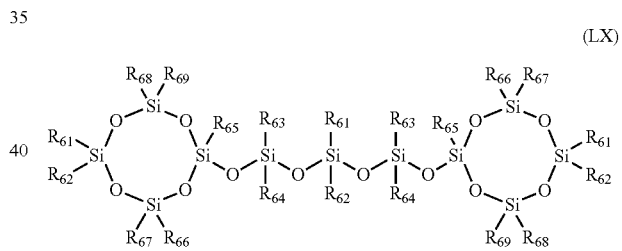

(LX)

wherein $R_{61}$ and $R_{62}$ are independently selected from the group consisting of haloalkyl groups, aralkyl groups, aryl groups, substituted aryl groups, heteroaryl groups, and substituted heteroaryl groups; $R_{63}$, $R_{64}$, $R_{65}$, $R_{66}$, $R_{67}$, $R_{68}$, and $R_{69}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups.

35. The composition of claim 34, wherein $R_{61}$, $R_{62}$, and $R_{65}$ are independently selected from the group consisting of aryl groups.

36. The composition of claim 35, wherein $R_{61}$, $R_{62}$, and $R_{65}$ are phenyl groups.

37. The composition of claim 34, wherein $R_{63}$, $R_{64}$, $R_{66}$, $R_{67}$, $R_{68}$, and $R_{69}$ are independently selected from the group consisting of alkyl groups.

38. The composition of claim 37, wherein $R_{63}$, $R_{64}$, $R_{66}$, $R_{67}$, $R_{68}$, and $R_{69}$ are methyl groups.

* * * * *